US011990212B2

(12) United States Patent
Benjamin et al.

(10) Patent No.: US 11,990,212 B2
(45) Date of Patent: *May 21, 2024

(54) DISTRIBUTED COMPUTING SYSTEM FOR BLOOD PROCESSING PROCEDURES

(71) Applicant: FENWAL, INC., Lake Zurich, IL (US)

(72) Inventors: Grant Benjamin, Ingleside, IL (US); Alfons Conley, Evanston, IL (US); Art Marshall, Hawthorn Woods, IL (US); Dale Meixelsperger, Gurnee, IL (US); Doug Newlin, Wheaton, IL (US); Urmi Marshall, Carol Stream, IL (US); Rebecca Lauseng, Lake Zurich, IL (US); Jonathan Prendergast, Chicago, IL (US)

(73) Assignee: FENWAL, INC., Lake Zurich, IL (US)

( * ) Notice: Subject to any disclaimer, the term of this patent is extended or adjusted under 35 U.S.C. 154(b) by 278 days.

This patent is subject to a terminal disclaimer.

(21) Appl. No.: 17/354,882

(22) Filed: Jun. 22, 2021

(65) Prior Publication Data

US 2021/0335459 A1 Oct. 28, 2021

Related U.S. Application Data

(63) Continuation of application No. 15/796,337, filed on Oct. 27, 2017, now Pat. No. 11,074,995, which is a
(Continued)

(51) Int. Cl.
*G16H 10/40* (2018.01)
*G06Q 10/0637* (2023.01)
(Continued)

(52) U.S. Cl.
CPC ......... *G16H 10/40* (2018.01); *G06Q 10/0637* (2013.01); *G06Q 10/087* (2013.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

| 2003/0004751 | A1 | 1/2003 | Ng et al. | |
| 2003/0018289 | A1* | 1/2003 | Ng | G16H 10/20 210/782 |

(Continued)

OTHER PUBLICATIONS

Panagopoulou et al. 1997, "A computer based solution for blood transfusion centres; the case study of Greece," Proceedings of Computer Based Medical Systems, Maribor, Slovenia, 1997, pp. 92-97, doi: 10.1109/CBMS.1997.596415.*
(Continued)

*Primary Examiner* — Robert W Morgan
*Assistant Examiner* — Charles P Coleman
(74) *Attorney, Agent, or Firm* — Becker Patent Law, LLC

(57) ABSTRACT

A distributed computing system for managing blood processing procedures in a blood processing facility has a system server, a plurality of computerized blood collection instruments and a computer. The system server stores data identifiers for different human operators. The blood collection instruments collect blood components from donors to generate collected products. Each instrument transmits data regarding the instrument to the system server, the system server storing data identifiers for each instrument. The computer presents the data regarding the blood collection instruments on a display and receives assignments of different donors to different blood collection instruments from a human administrator.

19 Claims, 9 Drawing Sheets

Related U.S. Application Data continuation of application No. 12/545,576, filed on Aug. 21, 2009, now abandoned.

(60) Provisional application No. 61/149,539, filed on Feb. 3, 2009, provisional application No. 61/091,187, filed on Aug. 22, 2008.

(51) Int. Cl.
*G06Q 10/087* (2023.01)
*G16H 10/60* (2018.01)
*G16H 20/40* (2018.01)
*G16H 40/20* (2018.01)

(52) U.S. Cl.
CPC .............. *G16H 20/40* (2018.01); *G16H 40/20* (2018.01); *G16H 10/60* (2018.01)

(58) Field of Classification Search
CPC ........ G16H 20/13; G16H 20/17; G16H 30/00; G16H 40/00; G16H 50/00; G16H 70/00; G16H 20/40; G16H 40/20; G16H 10/60; G16H 80/00; G06Q 50/22–24; G06Q 10/0637; G06Q 10/087
USPC ................................... 705/2, 3, 20
See application file for complete search history.

(56) References Cited

U.S. PATENT DOCUMENTS

| | | | |
|---|---|---|---|
| 2003/0040835 A1 | 2/2003 | Ng et al. | |
| 2003/0040938 A1* | 2/2003 | Ng | G16H 15/00 705/2 |
| 2003/0069480 A1* | 4/2003 | Ng | A61B 5/150786 600/300 |
| 2003/0078805 A1* | 4/2003 | Ng | A61B 5/15003 705/2 |
| 2003/0154108 A1* | 8/2003 | Fletcher-Haynes | G16H 10/40 705/3 |
| 2005/0209883 A1* | 9/2005 | Fletcher-Haynes | A61M 1/0286 705/2 |
| 2006/0047188 A1 | 3/2006 | Bohan | |
| 2006/0052949 A1* | 3/2006 | Fletcher-Haynes | A61M 1/30 702/21 |
| 2014/0350450 A1 | 11/2014 | Case et al. | |

OTHER PUBLICATIONS

Li et al. 2005, "From Codabar to ISBT 128: Implementing Barcode Technology in Blood BankAutomation System," 2005 IEEE Engineering in Medicine and Biology 27th Annual Conference, Shanghai, China, 2005, pp. 542-545, doi: 10.1109/IEMBS.2005.1616468.*
Appeal Documents from U.S. Appl. No. 12/545,576, Appeal Brief, Examiner's Answer, Reply Brief, Decision on Appeal, Request for Rehearing, Decision on Request for Rehearing (92 pages).
Documents from U.S. Appl. No. 14/455,413, Notice of Allowance (dated Sep. 13, 2017) and Reply to Final Office Action (dated Aug. 2, 2017) (36 pages).
FDA Department of Health and Human Services, "Substantially Equivalent 510(k) Device Information," Wyndgate Technologies, SafeTrace TX, version 1.0, http://www.fda.gov/Cber/510ksumm/K980023S.htm, retrieved Dec. 18, 2008 (8 pages).
GAMBRO Vista Information Systems, "Summary of Safety and Effectiveness," http://www.fda.gov/cber/510ksumm/k020015s.pdf (4 pages).

* cited by examiner

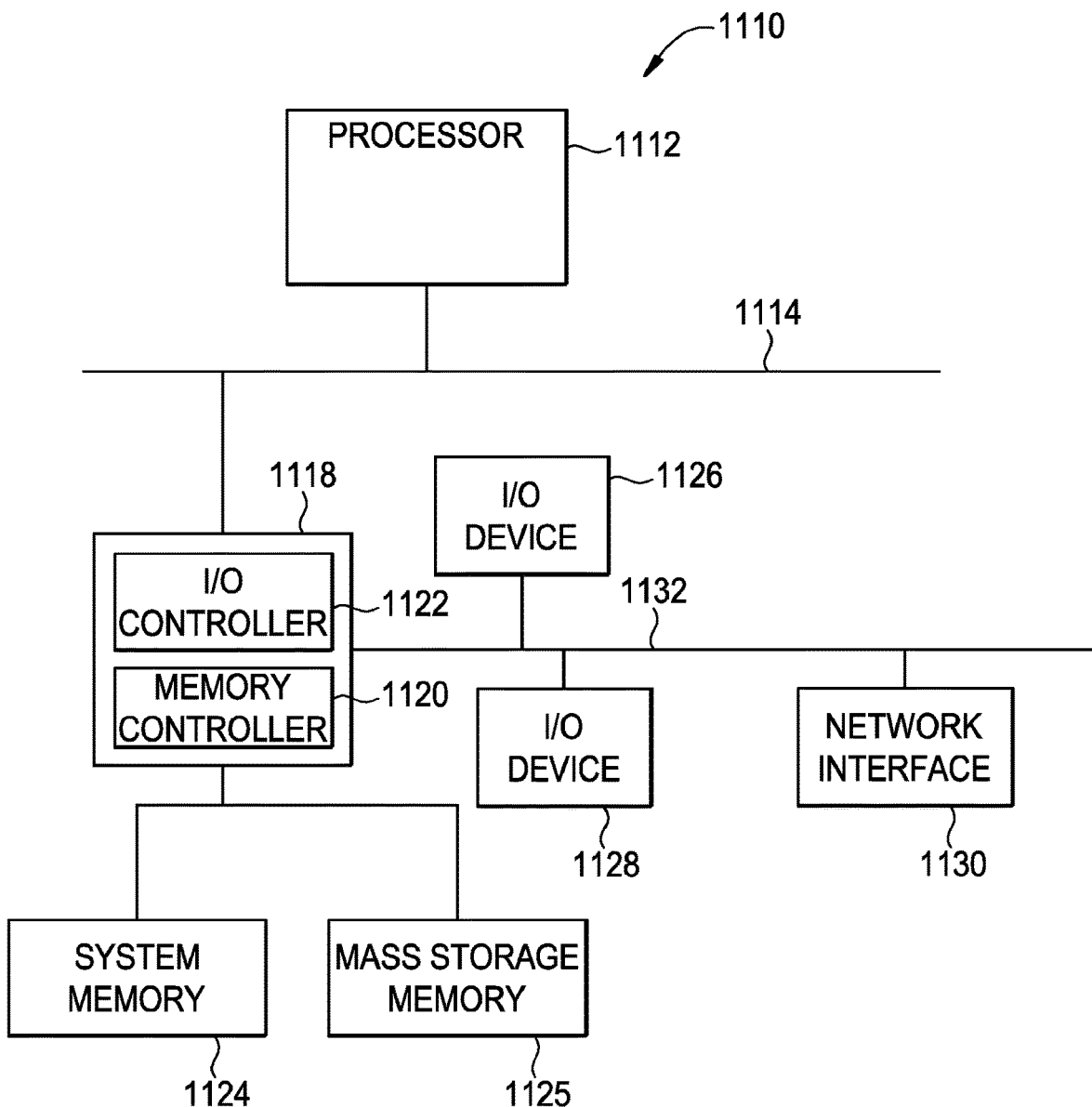

DISTRIBUTED COMPUTING SYSTEM FOR BLOOD PROCESSING PROCEDURES

CROSS-REFERENCE TO RELATED APPLICATIONS

The present application is a continuation of U.S. application Ser. No. 15/796,337, filed Oct. 27, 2017, which is a continuation of U.S. application Ser. No. 12/545,576 filed Aug. 21, 2009, which claims the benefit of U.S. Provisional Application No. 61/149,539 filed Feb. 3, 2009 and U.S. Provisional Application No. 61/091,187 filed Aug. 22, 2008, all of which are incorporated herein by reference in their entireties.

BACKGROUND

The present disclosure is directed to systems and methods for managing blood processing procedures. More particularly, the present disclosure is directed to operational and data management of blood processing procedures in one or more blood collection or processing facilities, or in the blood collection industry, generally.

Blood component therapy is a popular method of treating certain medical conditions or diseases. Blood components, such as red blood cells, white blood cells, platelets and/or plasma, can be removed from a patient's blood circulation to eliminate unhealthy components, or to collect healthy components for later administration to a further patient or recipient in need of such components. For instance, rather than transfusing a patient with whole blood, a patient can be given red cells, platelets, or plasma, depending on the condition being treated. For example, a patient suffering from anemia needs red cells, and treating that same patient with whole blood would be wasteful and could actually be detrimental to the patient. Plasma is often collected for further fractionation to obtain certain plasma proteins.

During a collection procedure, blood components commonly are removed from a patient's blood circulation by a process called apheresis. In this setting, it also would be appropriate to refer to the patient as a "donor". The removal of red cells and white cells is called cytapheresis or hemapheresis; removal of plasma is called plasmapheresis; and removal of platelets is called plateletpheresis.

During apheresis, intravenous (I.V.) lines are inserted into a donor's veins. Blood is drawn from the veins and transferred to a cell separator machine where the blood can be separated into component parts, such as by the process of spinning the blood in a centrifuge to collect various components of the blood. The speed of the centrifuge can be varied to isolate specific components by their density. Unneeded components can be returned to the donor/patient.

There are a number of facilities/organizations that are specifically set up to collect blood and blood components. Tracking donors, component handling, donor registrations, and the like are important aspects of the blood component collection industry. However, in the blood component collection industry there exist certain shortcomings in the areas of operational and data management for collection equipment, processes, collection centers and companies having a plurality of collection centers.

For instance, the current blood donation process generally includes the following steps. A donor arrives at a facility which typically will have a reception desk, a waiting room, a control desk, multiple collection bays, each commonly having six (6) collection instruments and beds operated by a phlebotomist or "operator", a soft goods or kit inventory storage area, a laboratory for testing or other treatment of collected products, a refrigeration area and a packaging and distribution area. The donor will check in at the reception desk. The donor's paper chart is pulled, or, if the donor is a new donor, a new chart is created. If available, the donor's donor management system (DMS) record is pulled and checked. Next, the donor signs in and is weighed, with the weight being recorded on the paper chart. A name tag with a barcode is printed for the donor. The donor proceeds to a screening area and is asked a series of medical questions. The answers given by the donor are recorded on the paper chart, with new donors having additional questions to answer. The donor's vital signs are checked and recorded on the paper chart. A small blood sample is taken from the donor and the protein level is measured, with the results entered on the donor's chart.

Next, the donor proceeds to the waiting room to wait to be called to the control desk. At this time, the donor's DMS record is updated with information from the paper chart. The collection facility designates for the donor a blood collection container and a blood collection kit, or other suitable collection device. A specific reference number to be associated with the particular donor's procedure, or "bleed number", is taken from a roll of preprinted barcode labels. There can be, for instance, three rolls of labels, each having different number ranges representing different blood types. The donor's name, donor number, and the date are printed on the appropriate label. Many labels are produced for each donor. One label goes on the donor's chart and several labels are applied to the collection kit and collection container. Some of the labels can later be removed and applied to smaller sample containers for testing or other purposes.

The donor then is escorted with the donor's chart, collection kit and container to an assigned bed in a collection bay where the donor's blood will be drawn. An operator sets up the donor with an instrument, collection kit and container and initiates the collection procedure. Upon completion of the collection, the actual volume of blood drawn from the donor is manually recorded on the collection container. After the donation is completed, the donor's chart and the container are transported to a processing desk. The collected blood can then be processed, such as for the removal of particular components, with the final product moving on to the refrigeration area to be placed in a freezer for preservation purposes. Eventually, the final product is moved to the packaging and distribution area for further handling, such as in the manner of packaging and shipment. This process is repeated dozens if not hundreds of times within any given blood collection facility which, depending on factors such as size, number of instruments and staffing, for example, can accommodate dozens of donors at a time.

There are blood centers that have managed to automate some of the common processes, such as donor registration, blood sampling, and product handling. There also have been some teachings with respect to the inclusion of healthcare devices in computer networks. For instance, U.S. Patent Application Publication No. 2003/0069480 (Kok-Hwee et al.) is directed to a system and method for networking blood collection instruments within a blood collection facility, and is incorporated herein by reference. Also incorporated by reference herein is U.S. Pat. No. 7,072,769 (Fletcher-Haynes et al.), which is directed to an extracorporeal blood processing information management system. U.S. Pat. No. 5,857,967 (Frid et al.) is directed to a healthcare device which includes a web server and medical information thereon, and which generates hypertext markup language (HTML) files on the fly for providing such information to a client at a remote location using a standard browser interface. Another example is provided by U.S. Pat. No. 5,891,035 (Wood et al.), which is directed to an ultrasonic diagnostic imaging system. The imaging system is capable of accessing images and information from internal and external databases by means of a web browser. Access to the images or information can be over a local network or over the Internet, and the browser can be used to pull in system preset data or reference images from a reference image library. However, prior suggestions tend to relate to automating some rudimentary record keeping and tracking of the blood collection process and resulting collected products.

Unfortunately, blood centers have lacked innovative methods of managing operations and data, and have failed to discover or implement ways to drive further enhancements in areas such as efficiency, productivity, recruitment of donors, and safety.

SUMMARY

The present disclosure is directed to systems, articles of manufacture, and methods for managing blood processing operations and data for one or more blood component collection facilities.

In some examples, in a blood component collection facility comprising a plurality of separately operable blood component collection instruments, a system for networking the blood component collection facility includes a system computer including a memory and a communication interface. The system computer is linked to a plurality of input devices for tracking donors, operators, soft goods, and blood component collection instruments with respect to one or more blood product collection procedures. The system computer is also linked to at least one administrative level computing device to monitor blood component collection activities throughout the blood component collection facility and to facilitate decision making with respect to allocation of at least one of donors, operators, soft goods, and blood component collection instruments based on information regarding at least one of donors, operators, soft goods, and blood component collection instruments.

In some example, an article of manufacture includes a computer readable storage medium, and executable program instructions embodied in the computer readable storage medium that when executed by a programmable system cause the system to implement a graphical user interface for blood component collection resource management. The interface includes a graphical depiction of a plurality of blood component collection areas in a blood component collection facility. Each depicted area includes one or more of a graphical indicator of blood component collection instrument status, a graphical indicator of blood component collection kit status, a graphical indicator of operator status, and a graphical indicator of donor status. The plurality of graphical indicators is to convey at least one of a progress and alert for a blood component collection procedure occurring or scheduled to occur in a blood component collection area of the blood component collection facility.

In some examples, a computer-implemented method of soft goods donation resource and data management for one or more blood collection facilities includes electronically processing available identification and status information related to one or more resources including blood collection devices, blood collection kits, blood donors, and blood collection device operators for one or more blood collection stations. The method also includes automatically analyzing each of the available identification and status information for each of the one or more resources according to one or more measurement criteria. The method further includes transforming the available identification and status information analyzed for the one or more blood collection stations into a corresponding graphical indication of each of the available one or more resources. Additionally, the method includes electronically outputting the corresponding graphical indication of each of the available one or more resources for the one or more blood collection stations in a graphical user interface dashboard for user review. The method includes facilitating resource allocation and re-allocation based on the graphical user interface dashboard.

BRIEF DESCRIPTION OF DRAWINGS

FIG. 11 is a block diagram of an example processor system that can be used to implement systems, articles of manufacture, and methods described herein.

DETAILED DESCRIPTION

Figure 1:
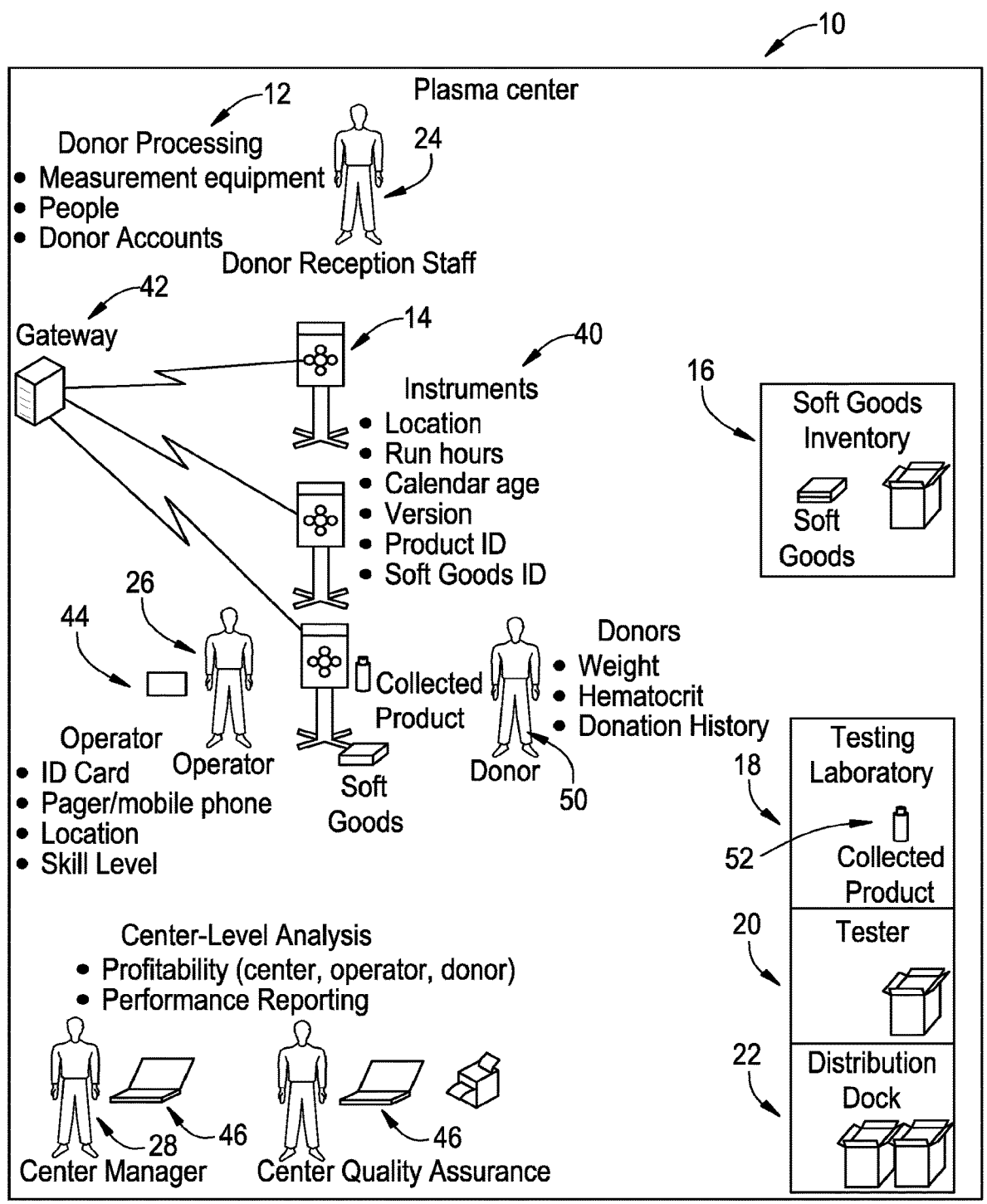
FIG. 1 is a schematic representation of an example system for managing blood processing procedures at a single collection facility.

The following description discloses examples of systems, articles of manufacture, and methods for managing blood processing procedures, which are susceptible of embodiments in many different forms. The present disclosures are not intended to limit the broad aspects of the invention.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements is hereby expressly defined to include a tangible medium such as a memory, a digital video disc (DVD), compact disc (CD), etc. storing the software and/or firmware.

The present disclosure is directed to systems and methods for managing blood processing procedures. This is stated in a broad sense which is intended to include further use and manipulation of data associated with blood processing procedures and the instruments, soft goods, donors, collected products, administrators, operators and facilities related to such procedures. For purposes of the present disclosure, the term "facility" or "center" will be used to refer to a location capable of biological fluid collection and/or processing via one or more collection or processing instruments. The facility and/or center can be a fixed and/or mobile facility/center, for example. Also, as used herein, the term "blood processing procedures" is intended to refer to any type of biological fluid collection, regardless of whether it includes the collection of blood or blood components.

In some examples, each blood component collection facility includes a plurality of separately operable blood component collection instruments, a facility administrator and a plurality of facility operators for administration of one or more blood component collection procedures involving one or more donors. The system generally includes a system server linked to the collection instruments.

The system server can include a communication protocol that facilitates communication between the system server and each of the plurality of blood collection instruments, and further can be linked to a headquarters (HQ) server, for an organization having more than one collection facility, as well as to a system of an outside entity, such as Fenwal, Inc., of Lake Zurich, Illinois, the supplier of instruments and soft goods, such as the collection kits used in the collection procedures.

The system server receives information or data, generally referred to hereafter collectively as "data", relating to blood component collections from one or more of the plurality of blood component collection instruments. The system server also can receive data associated with the placement, maintenance and status or other issues relating to the collection instruments. Data also can be received with respect to donors, administrators, operators, products collected, or related information, from mobile data transmission devices in the form of personal digital assistants (PDA's), such as a Palm Pilot™ by Palm, a PPT 2800 mobile computer by Symbol Technologies, or other handheld devices having scanning, bar code reading and/or key entry capability, or via "smart" devices, such as an RFID tag, smart card or comparable device to which data can be written and from which such data can be retrieved, or from input terminals, such as in the form of a desk top computer. The system server is adapted to store data in the system server memory and can be adapted to interact with outside network systems, such as a corporate system that is capable of pooling data from multiple collection facilities, systems of suppliers, such as Fenwal, Inc., or a system associated with other entities with which it can be desirable to link the system server.

The disclosed systems, articles of manufacture, and methods can be incorporated into an existing facility's system via an upgrade to existing hardware and software, or can be implemented in an entirely new facility that is equipped with devices more particularly designed for compatibility with the disclosed systems and methods. The present system provides a data connection between a collection facility's data management system, laboratory instruments, including, but not limited to, existing blood and blood component collection instruments, such as for example the Autopheresis-C® instrument which is supplied by Fenwal, Inc., the Fenwal CS-3000®, Amicus®, and/or Alyx® separators, also from Fenwal, Inc., and the instruments generally described in PCT Publication No. WO 01/17584, U.S. Pat. Nos. 5,581,687, 5,956,023, and 6,256,643, and biological treatment instruments, such as for example the pathogen inactivation instruments described in U.S. Pat. No. 7,025,877, which are all incorporated herein by reference.

Some example systems described herein lend themselves to automated tracing and/or tracking of several aspects of interactions with donors and utilization of a facility's assets. Numerous high level manipulations and uses of data are provided via integration of data from facility instruments, donors, administrators, operators, soft goods, and collected products. Recordation of data and event reporting can be further automated for strategic purposes, such as for enhanced safety, efficiency, productivity, profitability, value analysis, regulatory compliance, and the like, as discussed below in greater detail.

Some example systems are designed for a biological fluid collection and/or processing facility as an accessory to enhance the value and usefulness of the assets of such facilities, such as the instruments and personnel. The system can provide enhanced value at multiple levels within the blood collection business, based on improved operational and data management, with reduced manual data collection, and/or improved data manipulation.

Turning to FIG. 1, a schematic representation of an example collection facility 10 is shown as including a donor processing area 12 that includes a plurality of donor processing instruments 14, a soft goods inventory area 16, a testing and laboratory area 18, a refrigeration or freezer area 20, and a packing and distribution area or dock 22. The facility 10 further includes reception staff 24, operators 26, at least one administrator 28, and a first network 40. The first network 40 includes a system server 42 including a memory and a communication interface adapted to communicate with at least one wireless data interface, preferably a PDA 44, to accommodate several facility operators 26 and/or donors 50 at one time via wireless access. The first network 40 further includes data interface/computing devices 46, such as for running individual facility-level data analysis or quality assurance processing. The collection facility 10 is equipped to collect biological fluids, such as blood and/or blood components, from one or more donors 50, to generate collected products 52.

Figure 2:
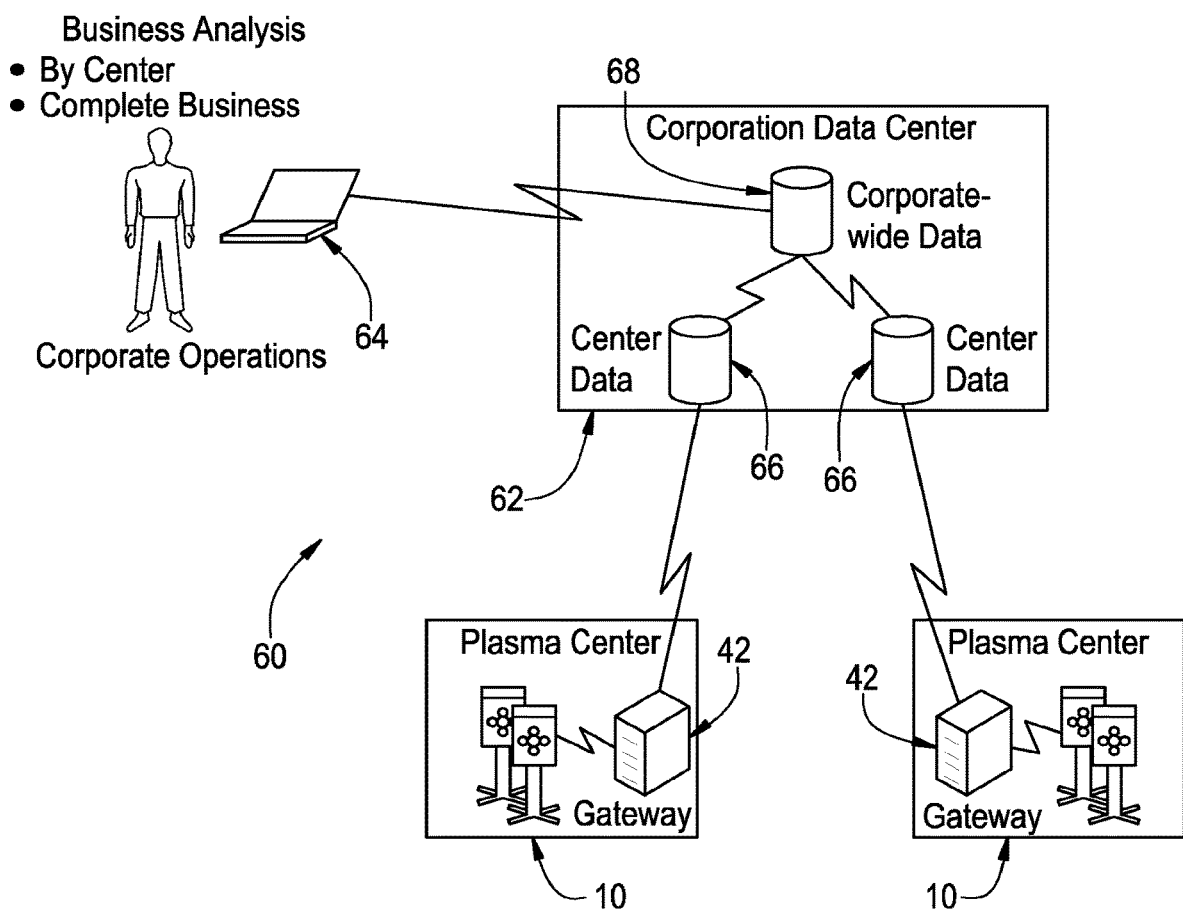
FIG. 2 is a schematic representation of an example system involving an entity that includes a plurality of collection facilities of the example type represented in FIG. 1.

Referring now to FIG. 2, it can be seen that a plurality of collection facilities 10 can be linked within a second network 60, as can occur with an entity that operates multiple collection facilities. Thus, the system can operate with a distributed set of databases. The second network 60 includes an HQ server 62 which is linked to each respective server 42 of the facilities 10, and to at least one HQ data interface/computing device 64 which can be used to conduct business analysis or other functions at an entity-wide level. The HQ server 62 generally can be located at a remote site from the collection facilities and/or the offices having the at least one HQ computing device, and can communicate with a first network at each respective facility and with the HQ computing device(s), such as via the Internet using a communication link such as a modem, digital subscriber line, or the like with a network switch, or as otherwise desired. The HQ server 62 can be configured to include storage of each respective facility's data 66, an aggregation of the facilities' data and any additional entity-wide data 68, which can for instance also include business records and the like, or other suitable data, as desired.

Figure 3:
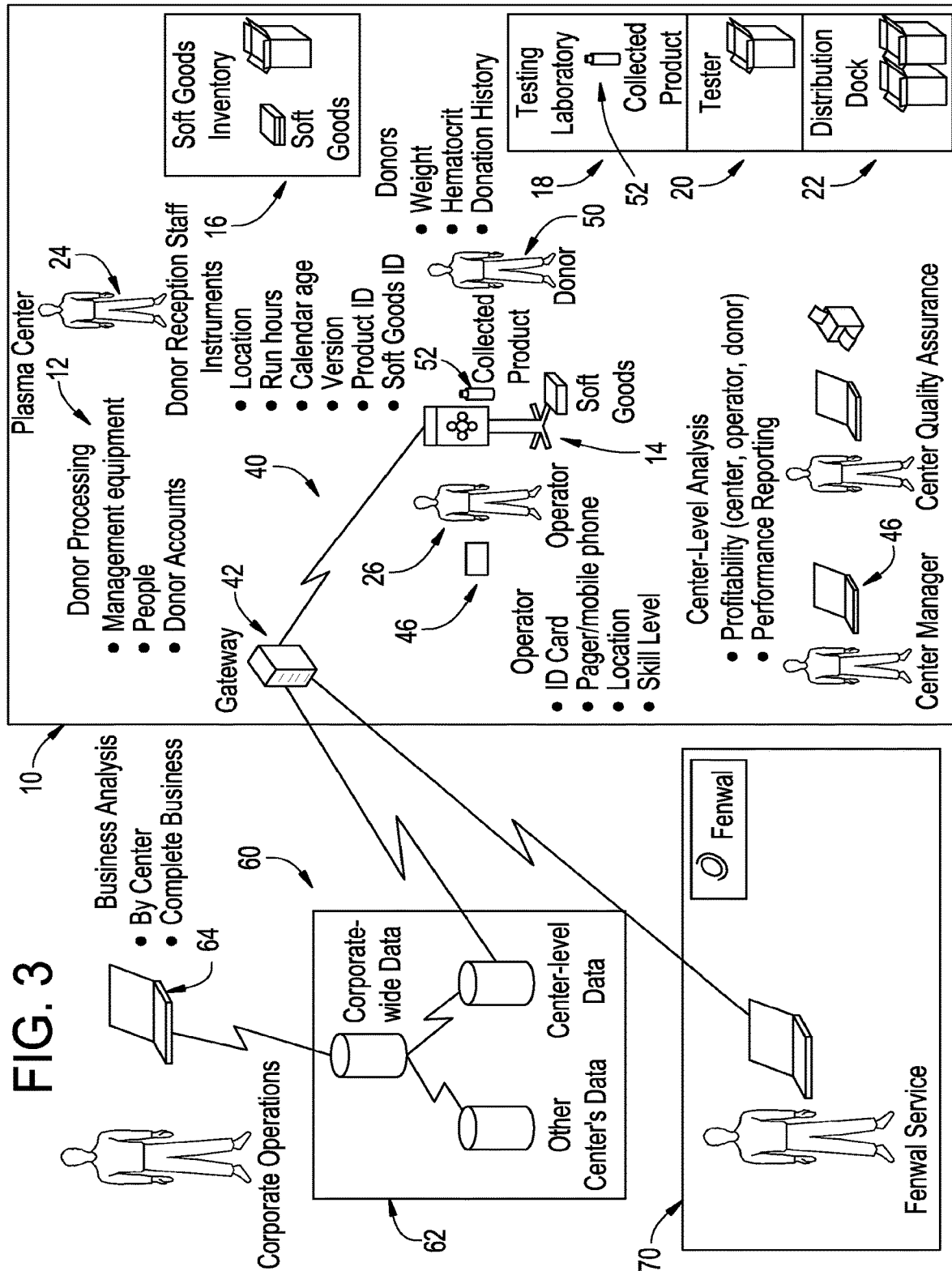
FIG. 3 is a schematic representation of a portion of an example system that includes the example entity having a plurality of collection facilities, such as that shown in FIG. 2, while also including an example link from a collection facility to a third party.

As represented in FIG. 3, the system server 42 of each respective collection facility 10 can be further linked to provide an interface with systems of third parties, such as is shown with respect to a computing system 70 of Fenwal, Inc. This linking can be at the level between the system server 42 of each respective collection facility 10 and the third party system 70, or can be between the HQ server 62 of an entity having multiple facilities and the third party system 70. Linking to one or more third parties can be particularly advantageous, as will be discussed below in more detail.

The first network 40 of a facility 10 includes hardware and software components and provides for inter-process communications. For instance, the reception staff 24 can intake information or data from donors 50 and upload that data via a computing device to the system server 42 directly, or to another device, such as a smart device, i.e. an RFID tag or other suitable medium which can travel with the donor 50. Additional data also can be uploaded, such as programming data for the instrument to be used, collection kit and container data, etc. The first network 40 also can communicate directly with the instruments 14, such as to program an instrument to run a selected procedure, and/or to receive data generated during a collection procedure. The operators 24 also can communicate data to the system server 42 via fixed computing devices and/or PDA's 44. This ability to link the facility personnel, instruments and data generated during procedures permits unique and highly useful operations and data management opportunities.

For instance, each operator 24 and instrument 14 is given a unique data identifier (ID). The unique data ID for each operator 24 permits accurate real-time tracking of an operator's location and activities. In addition, the operator ID can be used to link data with a given operator, such as relating to the operator's performance, certification for certain procedures, training or need for particular further training, ability to independently manage multiple collection procedures or to deal with particular alarm conditions, etc. The operator's data ID can be used to generate operator-specific prompts, based on skill or training levels, to better utilize the time of the operator. Additionally, other less technical data can be associated with an operator's ID, such as ability level to handle donors having difficult veins, compatibility with particular donors, etc. The operator's data ID also can be used to permit an appropriate access level to the facility's data for the individual operator. Such an operator-view of data can be customized for the particular type of display device to be used by the operator, such as for the screen of a selected PDA device.

The flow of information is transparent to the operator. The operator scans bar codes to receive the data ID's for the donor, collection kit and container, as well as for the apheresis instrument to set up the apheresis instrument for the collection procedure. The system server associates this data and creates a record for the donor bleed number and other respective data ID's associated with the procedure.

A unique data ID and tracking of events for each instrument 14 also can facilitate greater asset management. For instance, utilization data for each instrument can indicate greater use of particular bays or instruments relative to others, prompting a redistribution of procedures to maximize the life cycle of the facility's equipment. Instrument data associated with distinct data ID's also can be of assistance with respect to tracking problems or alarms associated with particular operating parameters, or scheduling for maintenance procedures or the like.

By utilizing unique operator and instrument data ID's, a facility administrator 46 can improve real-time asset utilization by optimally assigning donors across a facility's collection bays, while still appropriately stocking and staffing the bays with suitable instruments, collection kits and containers, and operators. Thus, the administrator can be proactive with respect to removing bottlenecks in the system that previously would have slowed the movement of donors and products through the facility. Further, such data can be used to better allocate particular instruments, operators or soft goods among different bays within a given facility or among multiple facilities. The data also can be used proactively to match staff and donor scheduling to better accommodate or eliminate peaks, and can be used to better select times for scheduled training of operators or maintenance of instruments.

An administrator 46 also will have an enhanced ability to strategically deploy operators to better balance the operator skill sets throughout the collection bays of a facility. The administrator further is better equipped to utilize the real-time data generated throughout the activities of the various areas within a facility 10 to move operators/personnel to those areas having the greatest immediate service needs, while also being able to select individuals that are qualified to render such services, or to be able to page the nearest qualified operator to respond to a given event, such as an instrument alarm mode. To facilitate such coordinated higher value decision making efforts, the administrator 46 can be permitted a manager-level view of the facility's data. The administrator-view of the data also can be customized for prompt access to different types of data, and for the particular type of display device to be used by the administrator, such as the screen of a stand alone computing device. An administrator can also configure operator view(s) for use in operator-specific task(s) and the computing device(s) and display(s) used for those tasks.

In addition to the unique operator and instrument data ID's, each donor 50 and each of the collection kits and containers, and the finished product containers 18 can receive a unique data ID. For proper traceability of all aspects of a procedure and resulting product, all information must be linked or synched with the apheresis instrument and the "bleed number." For instance, the use of donor data ID's, in addition to the benefits of automated association of the donor with the collection kit and container, also offers a potential to provide targeted donor education, such as an automated prompt to suggest viewing of an introductory video for new donors. Post donation education and donor care reminders also can be provided, such as messages to stay hydrated or take other actions. In addition, donor data can be used to provide an indication of whether a donor would be a good candidate to receive additional recruiting information for other procedures, or has already received such information. In this manner, effectiveness of donor messages and success rates of promotions also can be monitored.

This additional level of data also permits real-time tracking of the various processes and needs throughout the facility. It allows an administrator to better address and streamline the workflow through the facility to ensure proper handling of each respective donor, and that the product is being produced, handled and ultimately shipped in a timely, safe, and efficient manner. For instance, the viability of certain blood components can be affected by temperature. Accordingly, the system can be configured to track when a collection has been completed and when a container has reached its next stage of processing, and can provide an automated alarm if a container has not yet reached the next stage but is approaching a critical time for that next processing, or for example has reached a time by which it must be refrigerated. Thus, a container data ID located for instance on a bar code label, can be used to track the status of the container with respect to the initiation and completion of the donation, as well as post-donation status and location, and this information can be made available to operators or an administrator.

In other instances, such as with a mobile collection site, the real-time tracking of collections can facilitate better coordination and timing of the pickup of collected products, such as producing automated calls for a pick up of products based on the actual volume of collections, as opposed to predicted volumes. This further facilitates configuring the data management to provide automated soft goods and/or parts ordering.

At an organizational level, whether it be a stand-alone facility 10, or an entity operating multiple collection facilities 10, either has a unique opportunity to mine and utilize the data generated throughout their operations. This new system provides an opportunity for off-line analysis of utilization and performance data, measured via numerous parameters for each facility, instrument, operator, donor, collection kit and container.

In addition, the data can be analyzed with respect to yields, both predicted and actual. This can also be used in decisions with respect to donor recruitment, such as for example the need to recruit larger donors if yields are low.

The data can be configured to automatically provide an audit trail and/or documentary record for compliance purposes. It also can be configured for other automated functions, such as to trigger a particular promotion for recruitment of donors, or to flag a statistically significant issue to be addressed by facility/entity personnel, or by a third party, such as an unusual lot failure rate. The automated linking of data with particular collection kits and containers further removes the need to globally monitor a facility's use of a given lot of such devices, because all events associated with each such device now can be automatically tracked and identified with its original source lot.

The data analysis permitted with the example system further facilitates value and economic analysis. Thus, an entity can evaluate the particular value associated with each facility and instrument, and then further evaluate the value associated with each donor and operator. Such data permits analysis and generation of profit and loss statements on weekly, monthly or other periodic bases, and at the facility or multi-facility level. This data also can be used to reveal periodic trending or to predict the need for adding, removing or relocating particular facilities. Such data can further be analyzed on a macro level in conjunction with separately derived data relating to other aspects, for instance to environmental (weather, etc.) or community (local school schedules, etc.) aspects that can be affecting donation rates and recruitment.

The data can be further analyzed for predictive purposes, such as with respect to donor schedules, or potential success rates for targeted promotions relating to procedures needed to support particular types of therapies. With linking to the federal biovigilance system, the data would be useful to help in decision making with respect to how to target particular donors.

The link to third parties can be for supply ordering purposes, or can be related to substantive performance issues. Thus, a facility or multi-facility entity can find it beneficial to be linked to an organization, such as Fenwal, Inc., to provide information, analysis or consulting services. For instance, a facility could be linked to a third party instrument supplier system to receive service diagnostics reports, or automated real-time pop-ups in response to alarms. The link to the third party system also can be configured to download software updates for instruments, or the like. Statistical data could be gathered and shared with the third party to gain assistance in analyses, such as discussed above with respect to being otherwise undertaken at an entity level. Alarms or ongoing procedure data can be transmitted as well, to permit reduction in paper communications and the time required to receive an acknowledgment and suggested corrective action. This can be particularly helpful with respect to providing more immediate intervention, such as when a specific lot has been identified for discontinued use. Some of these benefits of providing a link to a third party will be experienced at an intermediate level where an entity operating multiple facilities is at least equipped to push information, updates or other data out to the individual facilities.

By use of smart devices, such as an RFID tag or preprogrammed smart card, an operator can be permitted to have an instrument be self-programming by merely presenting the smart device to the instrument for uploading of information. This can be useful for issuing software updates, or with respect to confirming that the correct collection kit and container and procedure have been uploaded for a specific donation.

In some examples, one or more integrated circuit card, smart card, and/or other portable processing device can be used to maintain donor parameters and run parameters and to program such information on one or more blood processing devices. For example, an integrated circuit card, smart card, and/or other portable processing device can be used to store and maintain donor information related to the physical characteristics of a given donor. The integrated circuit cards can also be used to store procedure parameters for a given donor. The integrated circuit card can then be used to program a blood processing device with the information stored on the integrated circuit card.

Certain examples lessen an operator's intervention with an apheresis device and allow for an enhanced data management and donor management system for blood collection facilities. By using an integrated circuit card and/or other portable processing device to program and maintain donor information, the burden on a blood processing device operator can be lessened. The operator can eliminate manual entry of each donor parameter or run parameter into the blood processing device and can instead use the integrated circuit card to program the blood processing device for operation. In addition, the operator and/or administrator can establish procedure criteria prior to the donor's arrival at a site and better allot for and maximize or optimize use of available blood processing device(s).

Integrated circuit cards, smart cards, and/or other portable processing devices can be used in different circumstances. Electronic cards can be used to program donor parameter(s) and also to store completed procedure parameters, for example. Smart cards can be single use or can be maintained such that each donor at a center has a smart card on which his or her donation history is stored.

An integrated circuit card, also referred to as a smart card, is a device containing an embedded integrated circuit wherein the card has the ability to process and store data. This technology can be applied to apheresis and blood processing devices to lessen the amount of interaction required by an operator and to enhance the data and donor management capabilities of a blood collection facility. Prior to a donation, a donor must go through a screening process at a given blood collection facility. At the time of this screening, as donor information is being recorded, and/or at a time prior to screening, information can also be stored onto an integrated circuit card. The integrated circuit card containing pertinent donor characteristics and procedure parameters can then be used by a given apheresis or blood processing device to program donor parameters and procedure parameters for a given procedure. Currently, apheresis and blood processing devices require an operator to enter the donor characteristics along with procedure parameters manually, often times through the use of a touch panel display. Using integrated circuit card technologies expedites pre-procedure setup on a given apheresis or blood processing device, in turn lessening the amount of time a donor waits and the burden on an operator. By lessening the burden on an operator, an opportunity to reduce the chances for human error is presented. The donor experience can also be heightened through the application of integrated circuit cards technology, as the time for the blood donation process can potentially be lessened, thus enhancing a donor's experience.

Integrated circuit cards can also be used to track and maintain information related to prior donations from a given donor. This information, stored on an integrated circuit card, can allow for a blood center administrator to set up devices with the expected procedure parameters prior to the donor's arrival at the center, thus allowing for more thorough planning of instrument utilization and optimization of collections form a given set of instruments. By storing donor information and procedure information onto an integrated circuit card, a blood center has an opportunity to track a donor's records and procedure history with greater ease.

Certain examples provide an "intelligent" dashboard for improving operational performance at and/or across blood collection facilities. An example system can include instruments providing procedure data, a donor management system providing donor data & characteristics, an operations database providing operator characteristics, and a dashboard with business logic to recommend operations actions. The system can be used, for example, in a donor center that manages multiple instruments that collect and/or process blood components. The dashboard uses information provided from the instruments, the donor management system, and characteristics about the operator to make recommendations to various staff members to improve operational efficiency in a donor center. The dashboard provides tools and guidance for a donor center to operate more efficiently by utilizing information available from instrumentation that collects and/or processes blood components.

Current practices in the field are based on human knowledge and observation, which can be error-prone and inaccurate, resulting in inefficient usage of the donor floor. Using the dashboard, communication and dissemination of information, as well as real-time calculation of key operational parameters, can be automated to help provide a more efficient operation. Donor centers process blood component donations by bringing donors into the donor center, screening the donor to ensure the safety of the collected component, assign the donor to a donation location, process the donation, including inserting a needle (or multiple needles, if applicable) into the donor's arm (a process called venipuncture) and completing the donation by removing the needle and providing the collected component(s) to another area for further processing. Using the dashboard, donor assignment and processing can be automatically facilitated in a more efficient manner based on available information and operational parameters, for example.

Figure 4:
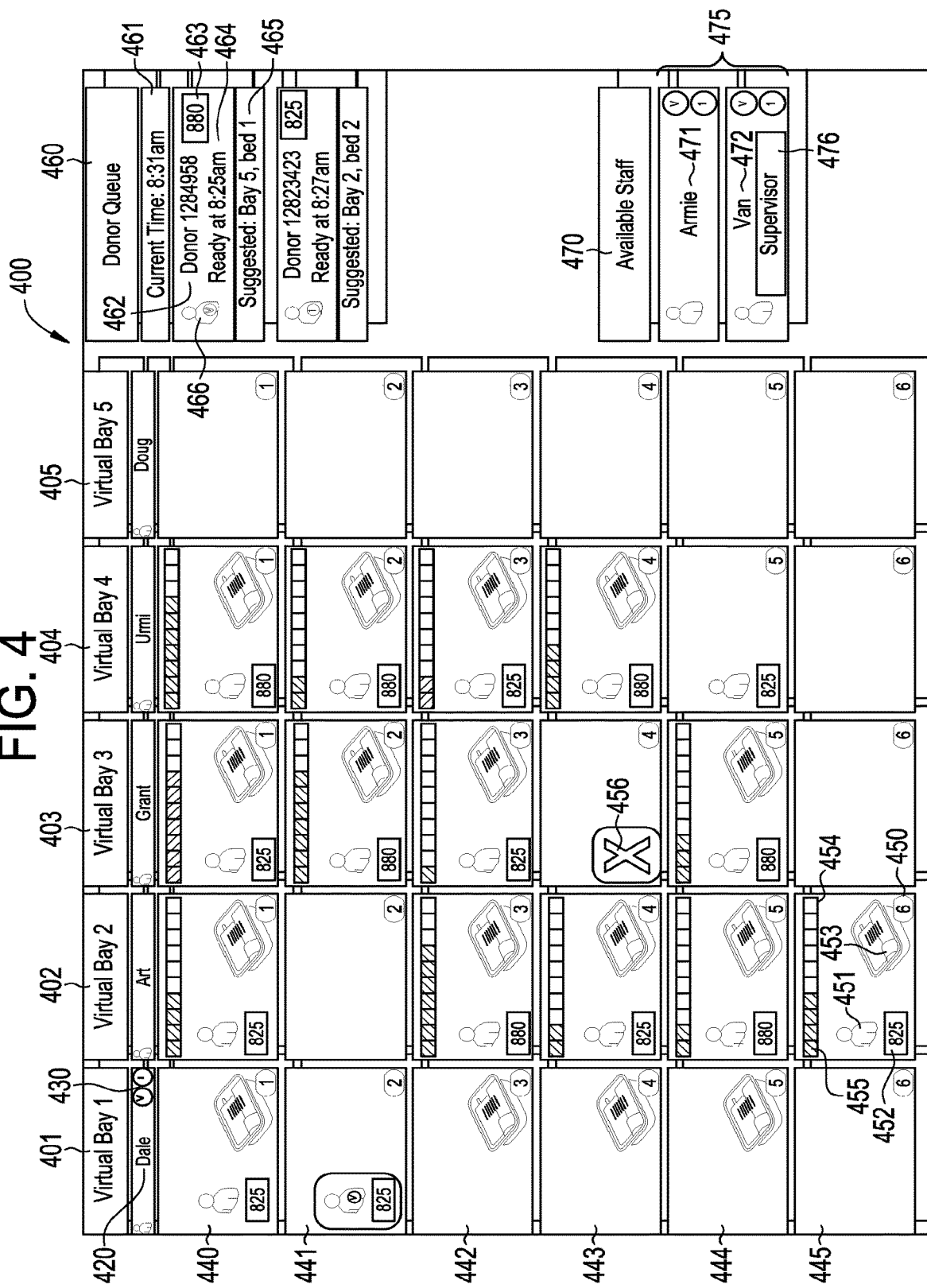
FIGS. 4-8 depict an example operations dashboards for a blood collection facility

As an example, FIG. 4 depicts an example operations dashboard 400. The dashboard 400 can be implemented, for example, at a control desk in a donor center or as a screen readable to the entire operations floor, such as on a large television in the donor area, on a portable computer carried by an operator, etc. The dashboard 400 provides information on the status of any donations in process, any donors waiting for donation (donor queue) and any staff available to assist any of the current staff (staff queue), for example.

Figure 5:
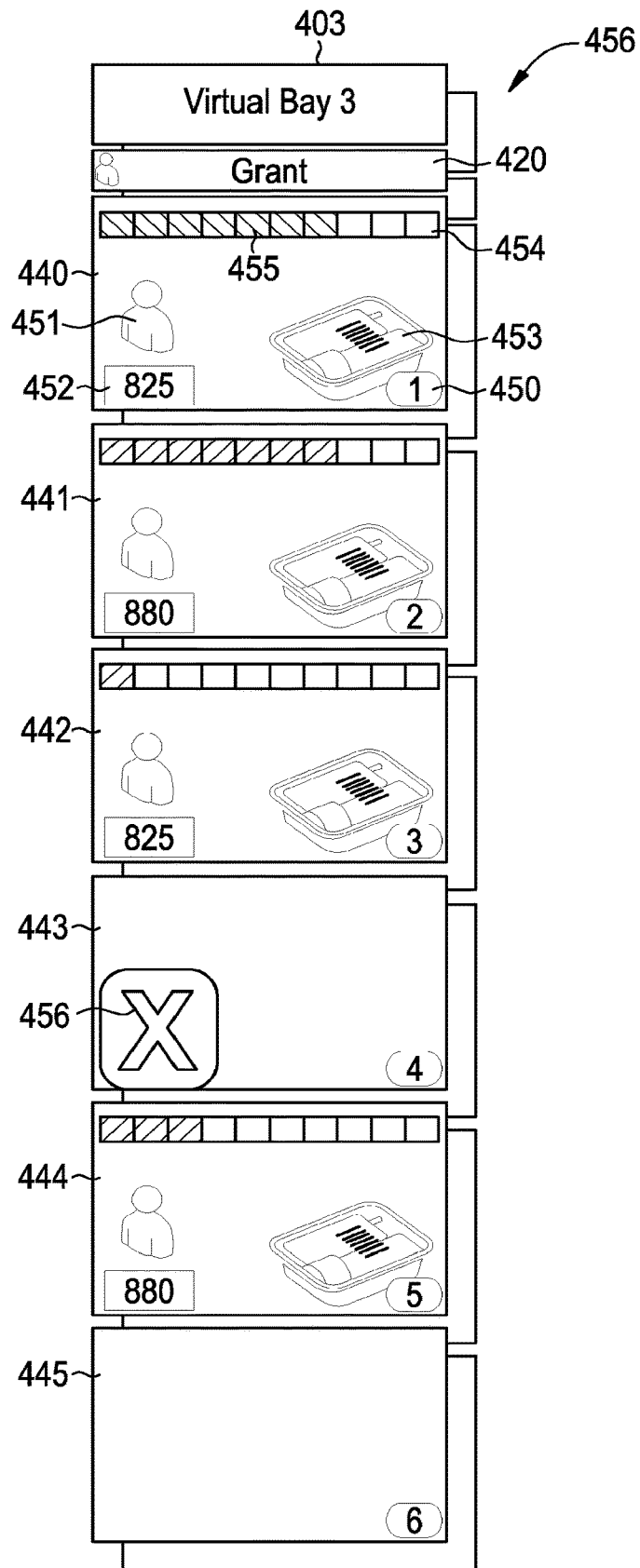

As shown, for example, in FIGS. 4 and 5, the dashboard 400 can be organized into virtual bays 401-405, which can or can not reflect the physical layout in the donor center. These virtual bays 401-405 illustrate the actual donations that are managed by an individual instrument operator or phlebotomist as well as an identifier 420 for the phlebotomist and an identification 430 of that phlebotomist's capabilities.

Figure 6:
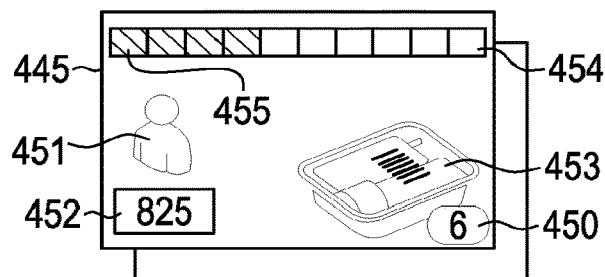

As shown in FIGS. 4, 5, and 6, each bay 401-405 includes one or more virtual beds 440-445 which represent a donation in progress. Each virtual bed 440-445 identifies the following characteristics: 1) a donation bed 450; 2) a donor presence 451; 3) a collection volume for the donor 452; 4) presence of an installed soft good set 453; 5) progress of the donation 454; and/or 6) a status of the donation 455, including any alarms or alerts, for example. For example, a number and/or other identifier can be used to indicate the donation bed 450 within a bay 401-405. A number and/or other identifier can be used to identify a collection volume for the donor 452. An alphanumeric and/or graphical indicator can identify the presence of an installed soft good set 453 (e.g., tubing, filter(s), collection bag(s), etc. for a machine such as a Fenwal Alyx, an Amicus, etc.) in a blood processing/collection system at the bed 440-445. A progress bar and/or other alphanumeric and/or graphical indicator can be used to represent the progress of a donation 454, and a graphical indicator (e.g., a color) and/or other representation can be used alone and/or in conjunction with the progress indicator 454 to provide a donation status 455, for example. An "X" and/or other similar indicator 456, for example, can indicate an unavailable bed.

Figure 7:
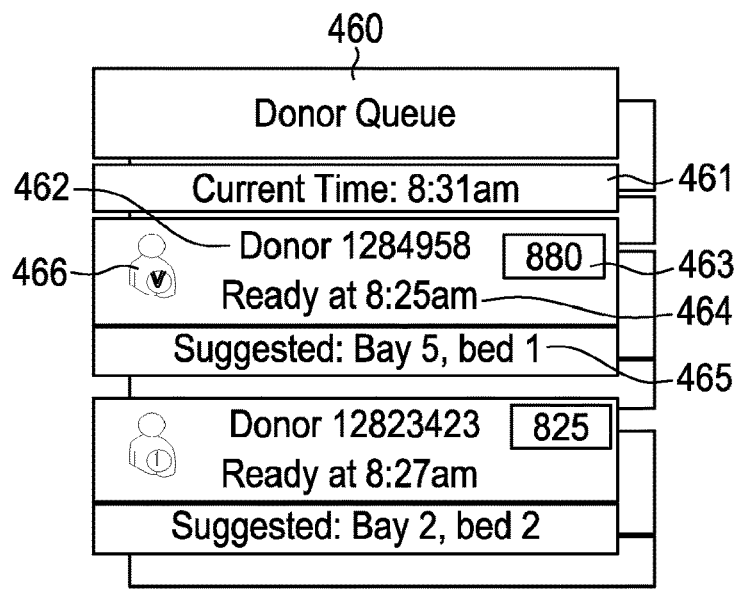

The dashboard 400 also includes a queue of donors 460 waiting to donate (see FIGS. 1 and 7). The donor queue 460 identifies a current time 461, the donor 462, the intended collection volume 463, the time that the donor arrived 464, and a suggested donation location 465. The queue 460 can also include an intended collection type 466, for example.

Figure 8:
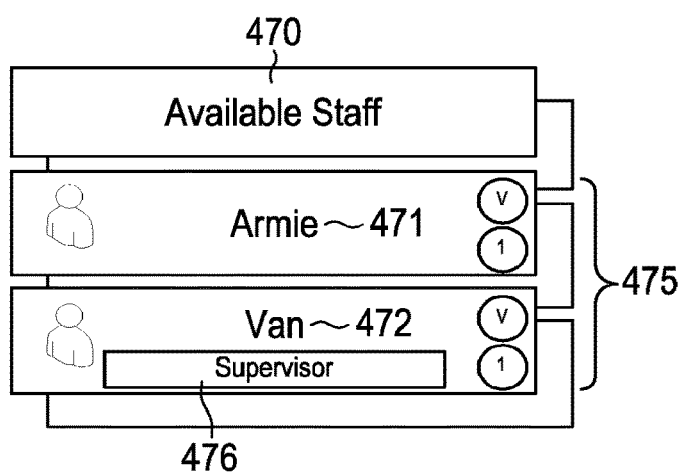

As shown in FIGS. 1 and 8, a staff queue 470 identifies which staff are available to assist the current donor floor staff. The staff queue 470 identifies the available staff 471, 472 as well as any specific capabilities 475, including specialized venipuncture skills and skills for handling first time donors, for example. The staff queue 470 can also highlight and/or otherwise identify 476 supervisory and/or other staff, for example.

This dashboard and associated data can also be used to collect aggregate information about the center operations and present the information to supervisory staff to improve operations. For example, real-time average collected component yield can be displayed to alert the supervisory staff to areas needing additional assistance to improve yield. The dashboard and associated data can be used to facilitate dynamic, real time (including substantially real time) allocation, reallocation, and maintenance of blood collection facilities and resources.

In some examples, pre-programmed collections are provided. Pre-programmed collections can be applied to any apheresis machine. For example, for return donors, all previous collection information can be pre-programmed into the apheresis device based on donor ID prior to a collection. All previous donations can be stored in a data management system, and when a donor has scheduled a donation, the donor information from prior donation can be downloaded onto the apheresis device including total blood loss for the year.

By pre-programming past collection information into a blood processing devices, operator input of incorrect donor information (e.g., height, weight, hematocrit, sex, etc.) on the day of collection can be reduced. An operator can pull up the donor's ID, and all prior entered donor information (e.g., sex, height, weight, hematocrit, etc.) and collection target information (if available) is then set for the blood processing device.

A verification can be shown with information such as donor's name, birth date, and picture, to help ensure that the operator entered the correct donor ID. An operator can make adjustments to parameters, such as weight, etc., and collection targets, if needed or desired.

The apheresis device tracks blood loss, components collected, etc., and at the end of a specified period (e.g., the day, the procedure, a certain amount of idle time, etc.), the data is uploaded into a data management system. Target or predicted collection volume (e.g., of whole blood cells, red blood cells, platelets, plasma, etc.) and actual collection volume can be collected and compared, for example. Thus, information can be shared between a data management system and the apheresis device through an interface.

In some examples, apheresis device collection information is automatically recorded and transmitted to a connected information system. The information system can be used to determine eligibility of a donor to donate various blood components based on donor history and donation guidelines for a particular donor and/or procedure.

Using the information system, a blood center can process a donor from initial check-in through completion of a blood collection procedure. Donor information and history is reviewed to determine that the donor is eligible to donate desired blood products based on donor information, donor history, and blood center policies. The information center can also help determine desired procedure and blood product(s) to be collected based on blood center needs, donor information, and donor history. An apheresis device can be programmed based on this information by downloading of configuration information from the information system to the apheresis device, transmission of instructions to a technician, programming of a smart card and/or other device for insertion in and/or other connection to the apheresis device, etc. The information center can store and update donor information, donation history, procedure data, laboratory data, and/or configuration settings, for example, to facilitate blood collection device programming and blood collection from a donor.

Figure 9:
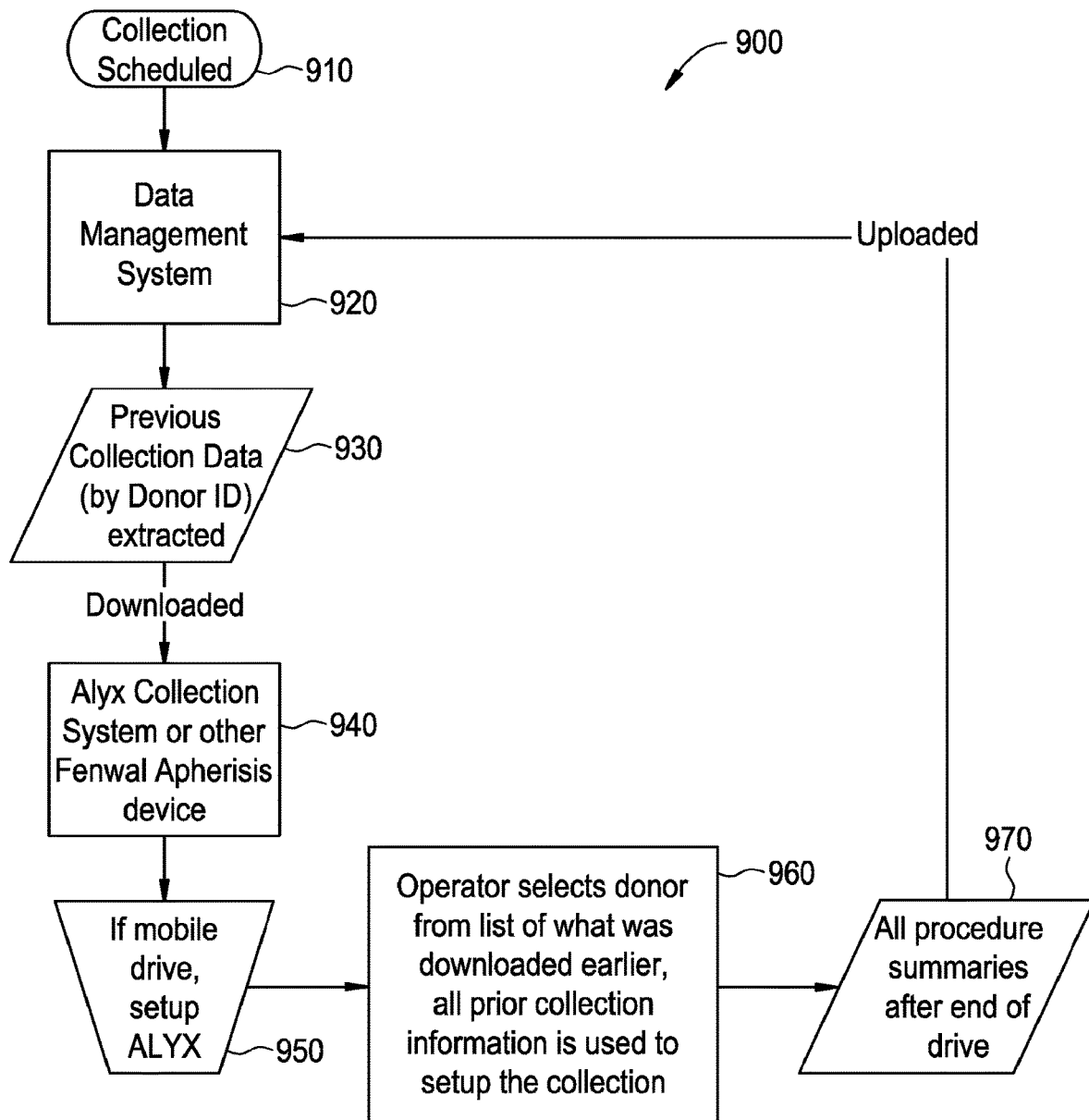
FIG. 9 is a flow diagram for an example method of donor blood product collection scheduling and configuration based on prior donor collection data.

FIG. 9 is a flow diagram for an example method 900 of donor blood product collection scheduling and configuration based on prior donor collection data.

At block 910, a collection is scheduled. The collection can be scheduled via phone registration, in-person appointment, and/or electronic scheduling, for example.

At block 920, a data management system receives the collection schedule. The data management system records the scheduled collection and updates a collection facility calendar, for example.

At block 930, the data management system extracts previous collection data based on one or more parameters, such as a donor ID. The data management system can retrieve one or more stored records of past donor activity, including donor physical information (height, weight, blood type, gender, age, etc.), donation habits, donation dates, preferences, etc. In some examples, previous donor collection data can be correlated and/or compared to current donation need(s), want(s), and/or other constraints, for example.

At block 940, the extracted previous collection data is downloaded to a blood processing device. For example, the data management system, directly and/or through a local computer system, can download configuration information to an apheresis device, such as an Autopheresis-C® instrument, CS-3000®, Amicus®, and/or Alyx® separator, to set up a blood collection for the donor.

At block 950, if a blood collection is a mobile collection, the mobile blood processing device is setup. For example, a mobile apheresis unit may require setup and installation at the collection site after being removed from its transportation packaging.

At block 960, an operator selects a donor from a list of downloaded donors at the blood processing device, and prior collection information is used to set up the collection. For example, the operator can be presented with a list of donors scheduled for the facility and can select the appropriate donor to configure the operator's machine for donation by that selected donor. Note that a single donor can be presented for machine configuration rather than selection from a list.

At block 970, after a blood collection and/or blood drive has been completed, procedure summaries are uploaded to the data management system. For example, actual yield, donor vitals, predicted yield, RBC/plasma loss, monitored device operation log information, etc. can be uploaded to the data management system for storage and/or analysis. Analysis can be used to drive future blood collection for this and/or other donors, resource reallocation, equipment modification, etc.

Figure 10:
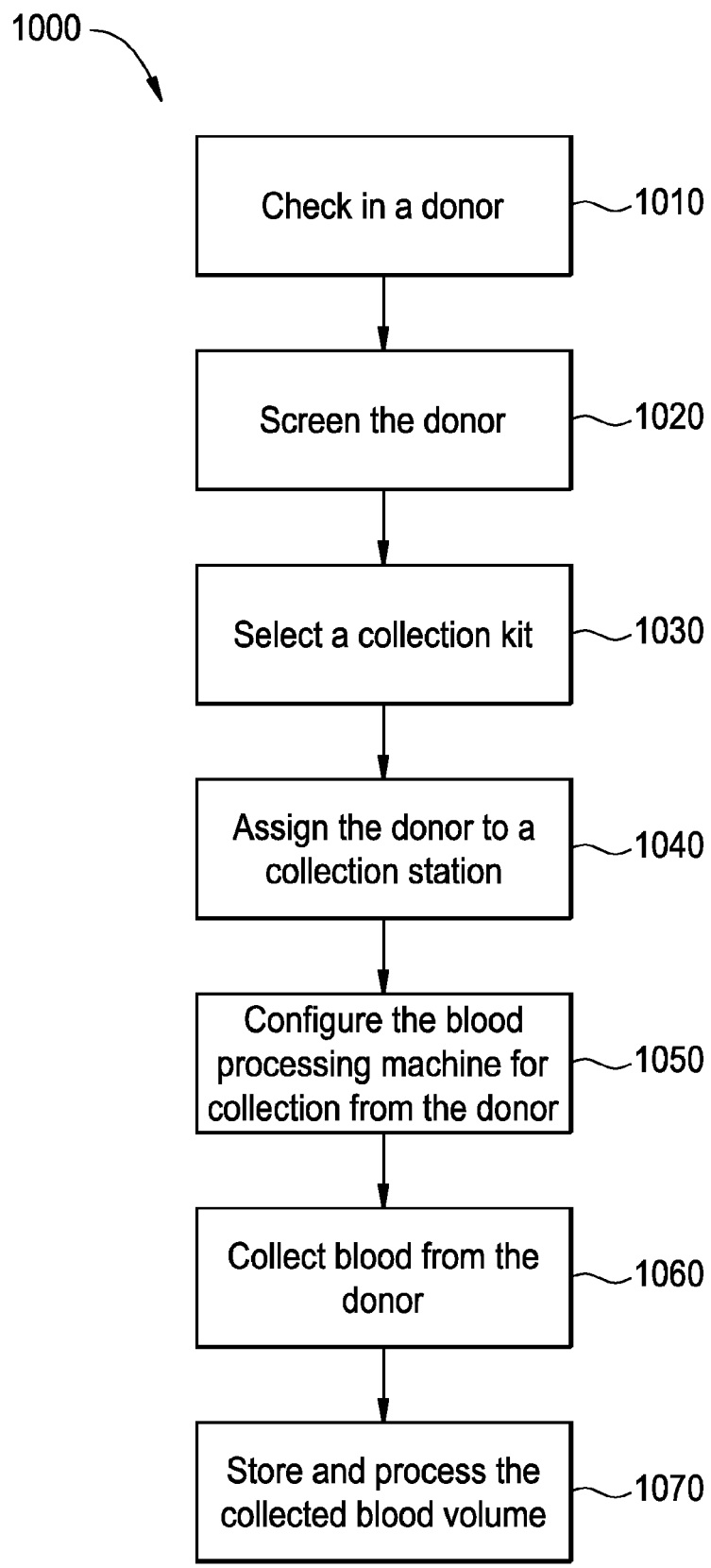
FIG. 10 is a flow diagram for an example method of donor registration and blood collection technician bay allocation for blood product collection.

FIG. 10 is a flow diagram for an example method 1000 of donor registration and blood collection technician bay allocation for blood product collection.

At block 1010, the donor checks in. For example, the donor can sign in electronically and/or via paper-based form. The donor's chart can be retrieved electronically and/or physically pulled from a file cabinet or shelf, for example. Donor identification, such as a card, badge, name tag, etc., can be generated. The identification can include a donor photograph, bar code, radio frequency identifier, and/or other identifier to identify the donor to the blood collection technician and/or blood collection machine, for example.

At block 1020, the donor is screened. Donor information, such as weight, temperature, protein level, other vital sign, etc., can be updated and/or otherwise recorded on the donor's chart.

At block 1030, a collection kit is selected for the donor. In some examples, the collection kit can have been previously selected and used to configure a blood collection device ahead of the donor's scheduled appointment. In some examples, the donor and the collection kit are taken to an assigned station for blood collection.

At block 1040, the donor is assigned to a collection station for blood collection. In some examples, assignment of a donor to a station is done in advance. In some examples, assignment of a donor to a station is done in real time after donor check in. Donor assignment to a station can be based on donor information and available station information, such as described above with respect to FIGS. 4-8.

At block 1050, a blood processing machine is configured for blood collection from the donor. The machine can be configured manually by an operator, via remote download from an external computer system, and/or locally via smart device, for example. Configuration can be based on graphical information such as the dashboards described in FIGS. 4-8 above, previous collection information, donor information, standard procedure configuration information, and/or other operating parameters, for example.

At block 1060, blood is collected from the donor. For example, based on a selected procedure (e.g., whole blood, plasma, platelets, red blood, etc.) one or more desired blood product(s) are collected based on a desired yield.

At block 1070, the collected blood volume is stored and processed. For example, an actual volume of blood product collected is noted (e.g., in writing and/or via electronic data input). The collected blood volume can be further processed for blood bank storage.

In some examples, alarms and/or alerts can be provided throughout the donor registration, blood processing device configuration, and blood collection process. An alert/alarm, collection machine status, donor status, etc., can be visually depicted on a dashboard, such as the dashboard of FIGS. 4-8, to indicate a state and/or level of concern. For example, a blue background can indicate that a machine is running A gray background indicates that a machine is ready and available for a donor to occupy, for example. A red background indicates a highest level of alert/alarm, for example. A yellow background indicates a medium level of alert/alarm, for example. An orange background can indicate that a donor has been sent to a blood collection machine and has been waiting longer than the allotted time. A white background indicates that the machine is off and not ready to be used for a donor.

In some examples, an icon or representation (e.g., donor representation 451) of a person can be shown in a collection bay to indicate the presence of a donor. A color and/or other indicator associated with the representation can indicate a state of the donor (waiting, collecting, in trouble, etc.). Alternatively or in addition, an icon or representation of a blood collection kit (e.g., soft goods kit 453) can be displayed via a dashboard (e.g., the dashboard 400) to indicate a kit status (e.g., installed, used, none installed, etc.). In some examples, a combination of donor 451 and kit 453 representations can together indicate the status of a collection bay 401-405. Additionally, a status bar (e.g., status of the donation 455) can be provided for a bay (e.g., 401-405) to indicate blood collection type, progress, alert/alarm, etc., based on color, pattern, and/or progress (e.g., progress of the donation 454) in the indicator bar, for example.

In some examples, data to be collected and stored, alerts/alarms, and/or other parameters can be predefined and loaded for an apheresis device and/or particular blood collection product. In some examples, data to be collected and stored, alerts/alarms, and/or other parameters can be defined and/or modified dynamically by a blood collection operator and/or apheresis device program. Alerts/alarms can be triggered for apheresis device—collection kit incompatibility, donor—blood collection procedure incompatibility, information system—apheresis device incompatibility, communication error, hardware error, software error, lack of operator responsiveness, lack of donor responsiveness, etc.

FIG. 11 is a block diagram of an example processor system 1110 that can be used to implement systems, articles of manufacture, and methods described herein. As shown in FIG. 11, the processor system 1110 includes a processor 1112 that is coupled to an interconnection bus 1114. The processor 1112 can be any suitable processor, processing unit, or microprocessor, for example. Although not shown in FIG. 11, the system 1110 can be a multi-processor system and, thus, can include one or more additional processors that are identical or similar to the processor 1112 and that are communicatively coupled to the interconnection bus 1114.

The processor 1112 of FIG. 11 is coupled to a chipset 1118, which includes a memory controller 1120 and an input/output ("I/O") controller 1122. As is well known, a chipset typically provides I/O and memory management functions as well as a plurality of general purpose and/or special purpose registers, timers, etc. that are accessible or used by one or more processors coupled to the chipset 1118. The memory controller 1120 performs functions that enable the processor 1112 (or processors if there are multiple processors) to access a system memory 1124 and a mass storage memory 1125.

The system memory 1124 can include any desired type of volatile and/or non-volatile memory such as, for example, static random access memory (SRAM), dynamic random access memory (DRAM), flash memory, read-only memory (ROM), etc. The mass storage memory 1125 can include any desired type of mass storage device including hard disk drives, optical drives, tape storage devices, etc.

The I/O controller 1122 performs functions that enable the processor 1112 to communicate with peripheral input/output ("I/O") devices 1126 and 1128 and a network interface 1130 via an I/O bus 1132. The I/O devices 1126 and 1128 can be any desired type of I/O device such as, for example, a keyboard, a video display or monitor, a mouse, etc. The network interface 1130 can be, for example, an Ethernet device, an asynchronous transfer mode ("ATM") device, an 802.11 device, a DSL modem, a cable modem, a cellular modem, etc. that enables the processor system 1110 to communicate with another processor system.

While the memory controller 1120 and the I/O controller 1122 are depicted in FIG. 11 as separate blocks within the chipset 1118, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 1110 of FIG. 11). When any of the appended claims are read to cover a purely software and/or firmware implementation, at least one of the components is hereby expressly defined to include a tangible medium such as a memory, DVD, CD, etc. storing the software and/or firmware.

FIGS. 9 and 10 include flow diagrams representative of machine readable and executable instructions or processes that can be executed to implement the example systems, apparatus, and article of manufacture described herein. The example processes of FIGS. 9 and 10 can be performed using a processor, a controller and/or any other suitable processing device. For example, the example processes of FIGS. 9 and 10 can be implemented in coded instructions stored on a tangible medium such as a flash memory, a read-only memory (ROM) and/or random-access memory (RAM) associated with a processor (e.g., the processor 1112 of FIG. 11). Alternatively, some or all of the example processes of FIGS. 9 and 10 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 9 and 10 can be implemented manually or as any combination(s) of any of the foregoing techniques, for example, any combination of firmware, software, discrete logic and/or hardware. Further, although the example processes of FIGS. 9 and 10 are described with reference to the flow diagrams of FIGS. 9 and 10, other methods of implementing the processes of FIGS. 9 and 10 can be employed. For example, the order of execution of the blocks can be changed, and/or some of the blocks described can be changed, eliminated, sub-divided, or combined. Additionally, any or all of the example processes of FIGS. 9 and 10 can be performed sequentially and/or in parallel by, for example, separate processing threads, processors, devices, discrete logic, circuits, etc.

One or more of the components of the systems and/or steps of the methods described above can be implemented alone or in combination in hardware, firmware, and/or as a set of instructions in software, for example. Certain embodiments can be provided as a set of instructions residing on a computer-readable medium, such as a memory, hard disk, DVD, or CD, for execution on a general purpose computer or other processing device. Certain embodiments of the present invention can omit one or more of the method steps and/or perform the steps in a different order than the order listed. For example, some steps can not be performed in certain embodiments of the present invention. As a further example, certain steps can be performed in a different temporal order, including simultaneously, than listed above.

Certain embodiments include computer-readable media for carrying or having computer-executable instructions or data structures stored thereon. Such computer-readable media can be any available media that can be accessed by a general purpose or special purpose computer or other machine with a processor. By way of example, such computer-readable media can include RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory can include read only memory (ROM) and random access memory (RAM). The computer can also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A distributed computing system for managing blood processing procedures in a blood processing facility, comprising:
    a system server including a memory and a communication interface, the system server configured to store data identifiers for a plurality of different human operators;
    a plurality of computerized blood collection instruments configured to collect blood components from donors to generate collected products, each blood collection instrument comprising a communication interface configured to transmit data regarding the blood collection instrument to the system server, the system server storing data identifiers for each blood collection instrument;
    a computer coupled to the system server and configured to present the data regarding the blood collection instruments on a display, to receive assignments of different donors to different blood collection instruments from a human administrator, and to configure operator-specific views or prompts for use in operator-specific tasks on the blood collection instruments or other computers using the data identifiers of the different human operators, the computer to determine at least one desired procedure and blood product to be collected based at least on donor data and to download configuration information to program one of the blood collection instruments for the at least one desired procedure, the one of the blood collection instruments collecting the blood product from a donor using the downloaded configuration information, wherein the downloaded configuration information comprises procedure information and/or operating parameters.

2. The distributed computing system of claim 1, further comprising:

a second system server disposed at a second blood processing facility remote from the first blood processing facility;

a headquarters server disposed at a third location remote from the first and second blood processing facilities;

a network configured to provide communication among the headquarters server, the first system server and the second system server; and a headquarters computing device in communication with the headquarters server configured to aggregate data from respective blood collection instruments at the first and second blood processing facilities for analysis.

3. The distributed computing system of claim 1, further comprising:

a third party system server in communication with the system server, the third party system server operated by a party not operating the blood processing facility, the third party system server configured to:

receive diagnostic reports from the blood collection instruments; and download software updates to the blood collection instruments.

4. The distributed computing system of claim 1, wherein the operator specific views or prompts are based at least in part on stored skill data indicating a skill of the operator.

5. The distributed computing system of claim 1, further comprising:

a plurality of handheld computing devices in communication with the system server for use by different human operators within the blood processing facility, the operator-specific view or prompts provided to the handheld computing devices according to the data identifiers associated with each respective human operator of the handheld computing devices.

6. The distributed computing system of claim 1, further comprising a smart device to automatically program the blood component collection instruments by presenting the smart device to the blood component collection instrument for uploading of configuration data to the blood component collection instrument.

7. The distributed computing system of claim 6, wherein the smart device stores donor data including donor parameters and run parameters to program the blood component collection instrument.

8. The distributed computing system of claim 1, wherein the computer presents a graphical dashboard for display to and interaction with a user, the graphical dashboard to provide a graphical depiction of the blood processing facility including an arrangement of blood component collection instruments, soft goods, operators, donors, and associated status information.

9. A distributed computing system for managing blood processing procedures in a blood processing facility, comprising:

a system server including a memory and a communication interface;

a first computer configured to receive donor data and upload the donor data to the system server;

a plurality of blood collection instruments, each blood collection instrument comprising a communication interface configured to transmit operation data regarding the blood collection instrument to the system server;

a source of blood collection kit status data;

a second computer coupled to the system server and configured to present a graphical depiction of a plurality of blood component collection areas in the blood processing facility, each depicted area representing a single blood collection instrument and comprising:

an indicator of blood component collection instrument status; and an indicator of blood component collection kit status;

the graphical depiction further conveying at least one of a progress and an alert for a blood component collection procedure occurring or scheduled to occur in at least one of the blood component collection areas of the blood component collection facility, wherein the distributed computing system is further programmed to configure one of the blood collection instruments via remote download of configuration data from the distributed computing system to the one of the blood collection instruments, the configuration data specifying at least a desired collection procedure, the one of the blood collection instruments collecting a blood component from a donor using the configuration data, wherein the downloaded configuration data comprises procedure data and/or operating parameters.

10. The distributed computing system of claim 9, further comprising a source of real-time operator status data, the real-time operator status data indicating which of a plurality of operators are available to assist a donor; the graphical depiction further depicting the real-time operator status data.

11. The distributed computing system of claim 9, further comprising a source of donor status data, the graphical depiction further depicting an indicator of donor status, wherein the graphical depiction further comprises a donor queue to indicate a suggested donation location among the blood component collection areas of the blood component collection facility for a donor in the donor queue.

12. The distributed computing system of claim 9, wherein the graphical depiction further comprises a staff queue to identify one or more blood component collection facility staff available to assist one or more operators in the blood component collection areas, the staff queue indicating one or more blood component collection capabilities of at least one staff in the staff queue.

13. The distributed computing system of claim 9, wherein the graphical depiction further comprises a donor queue to identify a plurality of donors waiting to donate blood, the donor queue indicating a time and an intended blood component collection for each donor.

14. The distributed computing system of claim 9, further comprising:

a second system server disposed at a second blood processing facility remote from the first blood processing facility;

a headquarters server disposed at a third location remote from the first and second blood processing facilities;

a network configured to provide communication among the headquarters server, the first system server and the second system server;

a headquarters computing device in communication with the headquarters server configured to aggregate data from respective blood collection instruments at the first and second blood processing facilities for analysis.

15. The distributed computing system of claim 9, further comprising:

a third party system server in communication with the system server, the third party system operated by a party not operating the blood processing facility, the third party system server configured to:

receive diagnostic reports from the blood collection instruments; and download software updates to the blood collection instruments.

16. The distributed computing system of claim 9, wherein the computer is further configured to automatically assign a donor to the one of the blood collection instruments based on the blood collection instrument status data and the donor data.

17. A distributed computing system for managing blood processing procedures in a blood processing facility, comprising:

a system server including a memory and a communication interface, the system server configured to store data identifiers for each of a plurality of blood collection instruments, the system server configured to receive intake donor data;

the plurality of computerized blood collection instruments configured to collect blood components from donors to generate collected products, each blood collection instrument comprising a communication interface configured to transmit to the system server availability data regarding whether the blood collection instrument is available for a procedure;

a computer in communication with the system server and configured to present the donor data and the availability data regarding the blood collection instruments on a display, the computer configured to assign a donor to a blood collection instrument based on the donor data and availability data;

wherein the system server is configured to retrieve previous blood collection data for a donor based at least in part on the donor data, to generate configuration data based at least in part on the previous blood collection data, and to remotely download configuration data to configure the assigned blood collection instrument for blood collection, the configuration data comprising at least a selected blood component collection procedure to be performed by the assigned blood collection instrument selected from a plurality of different blood component collection procedures, the assigned blood collection instrument collecting a blood component from the donor using the configuration data, wherein the downloaded configuration data comprises standard procedure information or operating parameters, wherein the computer is configured to automatically assign the donor to the blood collection instrument based on the donor data and availability data.

18. The distributed computing system of claim 17, wherein the system server is configured to store data identifiers for a plurality of different human operators and to present the data identifiers for the plurality of different human operators on a same display screen as the donor data and the availability data regarding the blood collection instruments.

19. The distributed computing system of claim 17, further comprising:

a second system server disposed at a second blood processing facility remote from the first blood processing facility;

a headquarters server disposed at a third location remote from the first and second blood processing facilities; and a headquarters computing device in communication with the headquarters server configured to aggregate data from respective blood collection instruments at the first and second blood processing facilities for analysis.

* * * * *